(12) United States Patent
Naganuma et al.

(10) Patent No.: US 6,287,118 B1
(45) Date of Patent: Sep. 11, 2001

(54) SHEET TYPE ORAL IMPLANT

(75) Inventors: Katsuyoshi Naganuma; Akira Kamiya; Akira Watatsu; Toru Nonami; Makoto Kato, all of Aichi (JP)

(73) Assignee: Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/393,269

(22) Filed: Sep. 10, 1999

(30) Foreign Application Priority Data

Sep. 10, 1998 (JP) .................................. 10-276538

(51) Int. Cl.⁷ ...................................................... A61C 8/00
(52) U.S. Cl. ............................................. 433/176; 433/173
(58) Field of Search ................................ 4733/172, 173, 4733/174, 175, 176

(56) References Cited

U.S. PATENT DOCUMENTS

| | | | |
|---|---|---|---|
| 3,579,829 | * 5/1971 | Sampson | 433/173 |
| 4,531,916 | * 7/1985 | Scantlebury et al. | 433/173 |
| 4,702,697 | * 10/1987 | Linkow | 433/173 |
| 5,133,662 | * 7/1992 | Metcalfe | 433/172 |
| 5,896,784 | 4/1999 | Kamiya et al. | 76/107.1 |

OTHER PUBLICATIONS

Kuintessensu Shuppan Kabushiki Kaisha, pp. 215–223, 242–252, "Chitan no Shikariyo", 1988.
Ishiyaku Shuppann Kabushiki Kaisha, pp. 14–23, "Chiyu no Byouri", 1997.

* cited by examiner

Primary Examiner—John J. Wilson
(74) Attorney, Agent, or Firm—Oblon, Spivak, McClelland, Maier & Neustadt, P.C.

(57) ABSTRACT

The present invention relates to a sheet type oral implant, and the present invention is an oral implant to be used by being secured on an alveolar bone, this oral implant is characterized by having a sheet portion whose shape on the bone side matches in an inverted convex-concave arrangement the surface shape of the alveolar bone; fixing hooks provided to the edges of the sheet portion and designed for securing the oral implant on the alveolar bone and preventing the implant from falling off; and a post portion for mounting an artificial tooth.

5 Claims, 5 Drawing Sheets

SHEET TYPE ORAL IMPLANT

BACKGROUND OF THE INVENTION

1. Field of the Invention

The present invention relates to an oral implant to be used to secure artificial teeth, which are used in place of lost natural teeth, in the oral cavity, and more particularly to an oral implant that imposes minimal physical stress on the patient during implantation, reduces the incidence of inflammation following implantation, and has other features.

2. Description of the Related Art

Oral implants are designed to secure artificial teeth, which are used in place of lost natural teeth, in the oral cavity. These oral implants are partially embedded and secured in the alveolar bone, and the artificial teeth are attached to the portions of the oral implants that are left to protrude into the oral cavity from the gums for this purpose.

Plate types, screw types, and perforated hollow cylinder types are widely used as oral implants. These are secured by being inserted partway in the alveolar bone. A drawback is that considerable physical stress is imposed on the patient during insertion of such oral implants, and postoperative inflammation or pain often accompanies the procedure because of unnecessary stress being induced in the alveolar bone. Gaps form between the oral implant and the bone, and the implant becomes loose as a result of mastication-induced cyclic stress, prolonged use, or the like, and bacteria penetrate into the gaps, causing inflammation. A resulting disadvantage is; that the oral implants must be replaced, and the alveolar bone itself is fractured.

SUMMARY OF THE INVENTION

The present invention provides a sheet type oral implant.

The present invention is an oral implant to be used by being secured on an alveolar bone, this oral implant comprising a sheet portion whose shape on the bone side matches in an inverted convex-concave arrangement the surface shape of the alveolar bone; fixing hooks provided to the edges of the sheet portion and designed for securing the oral implant on the alveolar bone and preventing the implant from falling off; and a post portion for mounting an artificial tooth.

With the present invention, minimal physical stress is imposed on the patient during the implantation of the oral implant, incidence of inflammation following implantation is reduced, the alveolar bone is prevented from being fractured when the oral implant is used, and other merits are provided.

DETAILED DESCRIPTION OF THE INVENTION

In view of the above and as a result of extended research on the use of titanium-based materials as biomaterials, the inventors perfected the present invention upon discovering that an implant can be adequately secured without being inserted into the bone.

Specifically, an object of the present invention is to provide an oral implant designed to fix an artificial tooth in the oral cavity.

Another object of the present invention is to provide an oral implant that imposes minimal physical stress on the patient during implantation, reduces the incidence of inflammation following implantation, and has other features.

Still another object of the present invention is to provide an oral implant that allows an implant to be secured without implantation into the bone.

Specifically, the present invention makes it possible to reduce the physical stress imposed on the patient during the implantation of an oral implant, to prevent the alveolar bone itself from being fractured during the use of the oral implant, and to solve other problems by providing an oral implant that comprises a sheet portion 2 shaped so as to cover an alveolar bone 4, fixing hooks 3 disposed at the tips of the sheet portion and designed for securing the implant on the alveolar bone and preventing the implant from falling off, and a post. portion 1 for mounting an artificial tooth, as shown in FIGS. 1 and 2; and by providing an oral implant configured as shown in FIGS. 4 and 5 and furnished with an auxiliary pin 9 designed to provide reinforcement and to prevent the implant from falling off the alveolar bone.

The present invention, which is designed to overcome the aforementioned shortcomings, comprises the following technical means.

(1) An oral implant, which is used by being secured on an alveolar bone, this oral implant comprising a sheet portion whose shape on the bone side matches in an inverted convex-concave arrangement the surface shape of the alveolar bone; fixing hooks provided to the edges of the sheet portion and designed for securing the oral implant on the alveolar bone and preventing the implant from falling off; and a post portion for mounting an artificial tooth.

(2) An oral implant, which is used by being secured on an alveolar bone, this oral implant comprising a sheet portion configured so as to cover the alveolar bone; fixing hooks provided to the edges of the sheet portion and designed for securing the oral implant on the alveolar bone and preventing the implant from falling off; and a post portion for mounting an artificial tooth.

(3) The oral implant set forth in (1) above, comprising the aforementioned sheet portion, fixing hooks, and post portion; and an auxiliary pin for reinforced mounting on the alveolar bone.

(4) The oral implant set forth in (2) above, comprising said sheet portion, fixing hooks, and post portion; and an auxiliary pin for reinforced mounting on the alveolar bone.

(5) The oral implant set forth in (1) or (2) above, comprising notches in the lateral sections of the sheet portion.

The present invention will now be described in further detail.

Aimed at overcoming the shortcomings described in the Description of the Related Art section, the present invention provides (1) an oral implant whose structure comprises a post portion for mounting an artificial tooth, a sheet portion whose shape on the bone side matches in an inverted convex-concave arrangement the surface shape of the alveolar bone, and fixing hooks for securing the oral implant on the alveolar bone and preventing the implant from falling off, as shown in FIGS. 1, 2, and 3; (2) an oral implant whose structure comprises a post portion for mounting an artificial tooth, a sheet portion configured so as to cover the alveolar bone with the proviso that the gap between the alveolar bone and the sheet portion be filled with bone cement during use, and fixing hooks provided to the edges of the sheet portion and designed for securing the oral implant on the alveolar bone and preventing the implant from falling off; (3) an oral implant comprising the structure of (1) above and an auxiliary pin designed to provide reinforcement and to prevent the implant from falling off the alveolar bone, as shown in FIGS. 4, 5, and 3; and (4) an oral implant comprising the structure of (2) above and an auxiliary pin designed to provide reinforcement and to prevent the implant from falling off the alveolar bone. Specifically, the present invention relates to an oral implant comprising a sheet portion whose shape on the bone side matches in an inverted convex-concave arrangement the surface shape of the alveolar bone; fixing hooks provided to the edges of the sheet portion and designed for securing the oral implant on the alveolar bone; a post portion 1 disposed substantially in the center of the sheet portion and designed for securing an artificial tooth; and, optionally, an auxiliary pin mounted and secured in a hole formed in the alveolar bone and endowed with the function of reinforcing the bond with the alveolar bone.

The present invention will now be described with reference to drawings. The drawings disclose preferred examples of the oral implant of the present invention.

The present invention is an oral implant configured as shown in FIGS. 1 and 2. This oral implant is used such that the fixing hooks 3 provided to all or parts of the tips of the sheet portion 2 are inserted into grooves (hereinafter referred to as "grooves in the lateral faces of the alveolar bone") bored in advance at prescribed positions in the lateral faces of the alveolar bone 4, and the oral implant is secured on the alveolar bone.

The oral implant shown in FIGS. 1 and 2 is used for mounting a single artificial tooth. The oral implant of the present invention may also by of a type designed for the mounting of a plurality of artificial teeth. The crosswise dimension of the sheet portion 2 (longest section of the sheet portion) in FIG. 2 falls within a range of 8 mm to 20 mm. The longitudinal dimension of the sheet portion 2 in FIG. 2 should fall within a range of approximately 5 mm to 10 mm, as measured to the left and right in FIG. 1 from the center of the post portion 1, which is disposed in the center of the curve on the sheet portion 2 in FIG. 1, including the fixing hooks 3. Increasing the two aforementioned dimensions of the sheet portion makes it necessary to make a larger incision in the gum area during the implantation of the oral implant, increasing the physical stress exerted on the patient and prolonging postoperative recovery. In addition, age promotes degeneration in the alveolar bone, and partial degeneration, deficiency, and the like are also observed. It is admissible in such cases for the sheet portion in FIG. 1 to be made with different lengths on the right and left sides as needed.

The oral implant shown in FIGS. 4 and 5 is obtained by providing the oral implant configured as shown in FIGS. 1 and 2 with an auxiliary pin 9 for providing reinforcement and preventing the implant from falling off the alveolar bone. A hole 10 must be drilled in the alveolar bone 4 in order to secure the auxiliary pin 9 to the alveolar bone. The auxiliary pin should be made smaller (diameter: 3 mm or less; length: 5 mm or less) to reduce the physical stress exerted on the patient during the drilling of the hole in the alveolar bone. FIGS. 4 and 5 depict a preferred example of the auxiliary pin, but this pin is not limited in any particular way in terms of shape, structure, the position at which the auxiliary pin is provided to the sheet portion, or the like as long as the pin can be secured in the hole formed in the alveolar bone. The auxiliary pin is secured using bone cement or the like. In particular, the auxiliary pin is required when the patient involved has a weak alveolar bone.

To allow the oral implant of the present invention to demonstrate its effects fully, it is preferable for section of the sheet portion 2 facing the bone to have a shape that matches in an inverted convex-concave arrangement the shape of the alveolar bone. The fixing hooks 3 inserted into the grooves in the lateral faces of the alveolar bone play the role of securing the oral implant on the alveolar bone. Providing the section of the sheet portion facing the bone with a shape that matches in an inverted convex-concave arrangement the shape of the alveolar bone has the effect of preventing movement by an outside force applied to the post portion 1 because this force is now countered not only by the fixing hooks but also by the entire contact surface between the sheet portion and the alveolar bone.

The shape of the alveolar bone varies from person to person and from location to location, so the oral implant can be fashioned by casting, superplastic forming, powder metallurgy, mechanical working, or other means on the basis of images taken from the areas surrounding the alveolar bone on which the oral implant is to be secured such that the section of the sheet portion facing the bone has a shape that matches in an inverted convex-concave arrangement the shape of the alveolar bone. The post portion is formed in the center of the bend on the sheet portion, as shown in FIG. 1. It is also possible to fabricate the sheet portion and the post portion separately and to integrate them into a unitary structure by soldering, adhesive bonding, or another existing joining technique.

As shown in FIG. 3, a fixing hook 3 must be configured such that the angle 7 between the sheet portion 2 and the fixing hook is 90 degrees or less. The length of the upper surface 8 thereof should fall within a range of 0.5 mm to 2 mm. The fixing hooks are not limited in any particular way and may be configured differently as long as the above-described conditions are met.

An artificial tooth is mounted on the post portion.

Although the post portion for mounting an artificial tooth is shown as a square pole in the drawings, the shape thereof is not limited to this square pole and includes cylinders, ellipses, triangular poles, pentagonal poles, and other polygonal poles. It is also possible to use shapes of variable sizes and shapes that are partial combinations of the above-described shapes. The length of the post portion varies with the thickness of the gums in the implantation area while remaining within a range of 3 mm to 10 mm. It is also possible to provide the post portion with an external or internal thread, and to mount artificial teeth by means of an internal thread if the post portion has an external thread, and vice versa.

Examples of materials that can be appropriately used for the present oral implant include pure titanium, titanium alloys, stainless steel, cobalt alloys, nickel alloys, and gold alloys, although any suitable material can be used as long as it provides the same effects. The sheet portion should be strong enough to withstand fracture, deformation during use, or deformation developed when the implant is secured over the lateral faces of the alveolar bone, so the thickness of the sheet portion may range from 0.3 mm to 1.5 mm.

The oral implant of the present invention is mounted by a technique in which force is applied at a prescribed location to the alveolar bone from the post portion in the direction of the alveolar bone, and the fixing hooks are forced into the grooves on the lateral faces of the alveolar bone. The term "prescribed location" refers to the location at which the shape of the alveolar bone and the shape of the section of the oral implant facing the bone are inverted relative to each other in a matching convex-concave arrangement. The presence of the fixing hooks makes it necessary for the sheet portion of the oral implant to temporarily expand when the oral implant is snapped onto the lateral faces of the alveolar bone. The notches 5 on the lateral sections of the sheet portion in FIG. 2 are provided in order to facilitate such temporary expansion during fitting. The temporary expansion during fitting is facilitated by increasing the length of the notches or reducing the intervals between the notches. An increase in the length of the notches or a reduction in the interval between the notches lowers strength during use, so the length of the notches must be limited to no more than 5 mm, and the interval between the notches should be limited to no less than 1 mm. In addition, narrower notches increase the area occupied by the fixing hooks, so the notch width should be 1 mm or less when two or more of them are provided.

The present invention also allows the use of a sheet portion whose shape does not match that of the alveolar bone. In the present invention, the sheet portion is not limited to one whose shape on the bone side matches in an inverted convex-concave arrangement the surface shape of the alveolar bone, and a sheet portion in which these do not match with each other may also be used. In this case, a sheet portion of any shape, structure, or the like can be used as long as the sheet portion is configured such that it can cover the alveolar bone. In the case of an oral implant whose sheet portion does not match the surface shape of the alveolar bone, the disparity between the alveolar bone and the shape of the section of the sheet portion facing the bone can be compensated for by filling the gaps between the bone and the dental root with bone cement, silicate cement, or the like in order to eliminate the difference in shape between the alveolar bone and the oral implant. Such filling can have substantially the same effect as that afforded by an oral implant whose shape matches the surface shape of the alveolar bone in an inverted convex-concave arrangement.

It is possible to secure an oral implant on the alveolar bone or to mount an artificial tooth on the post portion either by a method in which the artificial tooth is mounted on the post portion after the oral implant has been secured on the alveolar bone, or a method in which the oral implant is secured on the alveolar bone after the artificial tooth has been mounted on the post portion.

An oral implant having two or more post portions for mounting two or more artificial teeth can be fabricated by increasing the crosswise dimension of the post portion of an oral implant having a single post portion.

DESCRIPTION OF THE SYMBOLS

Figure 1:
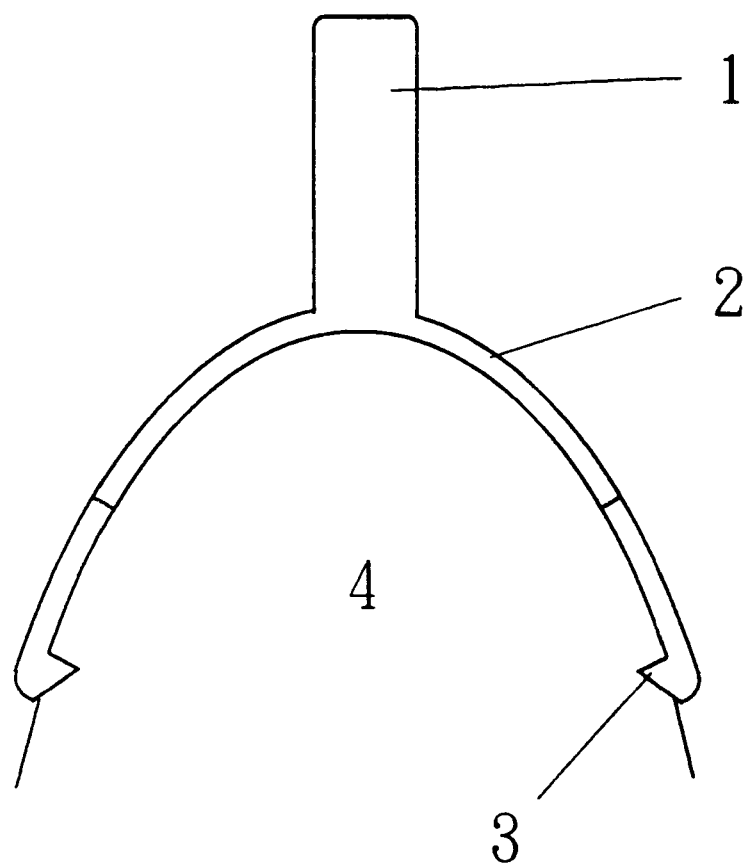
FIG. 1 is a cross-sectional view of the oral implant of the present invention.
Figure 4:
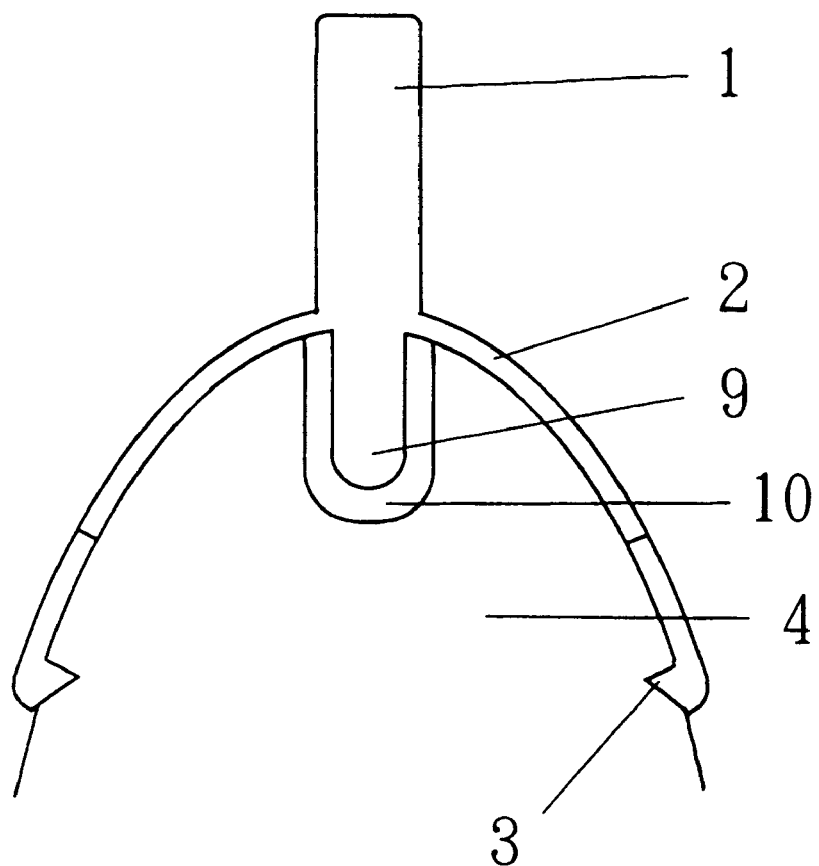
FIG. 4 is a cross-sectional view of the oral implant having an auxiliary pin in accordance with the present invention.
Figure 5:
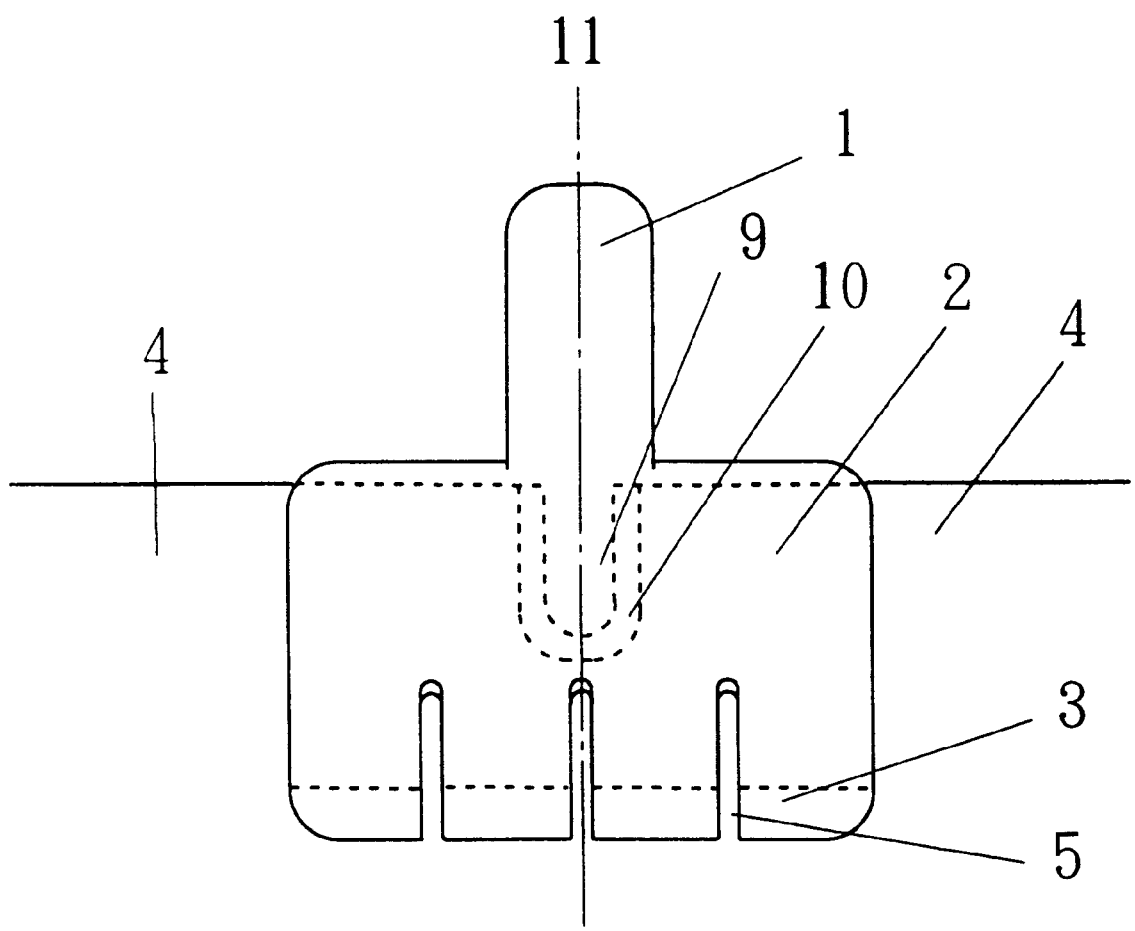
FIG. 5 is a lateral view of the oral implant having an auxiliary pin in accordance with the present invention.

1: post portion (cross section in the center in transverse direction is rectangular)
2: sheet portion
3: fixing hook
4: alveolar bone
5: notch
6: cross section in FIG. 1
7: angle between sheet portion and upper surface of fixing hook
8: upper surface of fixing hook
9: auxiliary pin (cross section in the center in transverse direction is circular)
10: insertion hole for auxiliary pin
11: cross section in FIG. 4

DESCRIPTION OF THE PREFERRED EMBODIMENTS

The present invention will now be described in detail through embodiments, but the present invention is not limited in any way by these embodiments. In the embodiments that follow, the symbols will refer to the symbols in the drawings.

Embodiment 1

In this embodiment, a bovine bone was processed to obtain a bone (hereinafter referred to as "the bone") whose shape resembled that of the alveolar bone, and this bone was used to evaluate the performance of the oral implant of the present invention.
1) Fabrication of Oral Implant A post portion of prescribed shape, fixing hooks, and, optionally, a flat substrate blank for a sheet portion having an auxiliary pin were fabricated using a milling machine, a lathe, or the like in accordance with a superplastic forming technique, and this substrate workpiece was molded to a prescribed shape using a ceramic mold created using images as a basis, yielding an oral implant. In the present invention, an oral implant with a sheet portion whose shape on the bone side matched as an inverted convex-concave arrangement the surface shape of the alveolar bone was fabricated on the basis of images of the bone by a superplastic forming technique in which pure titanium was used as the material for the oral implant.

Figure 2:
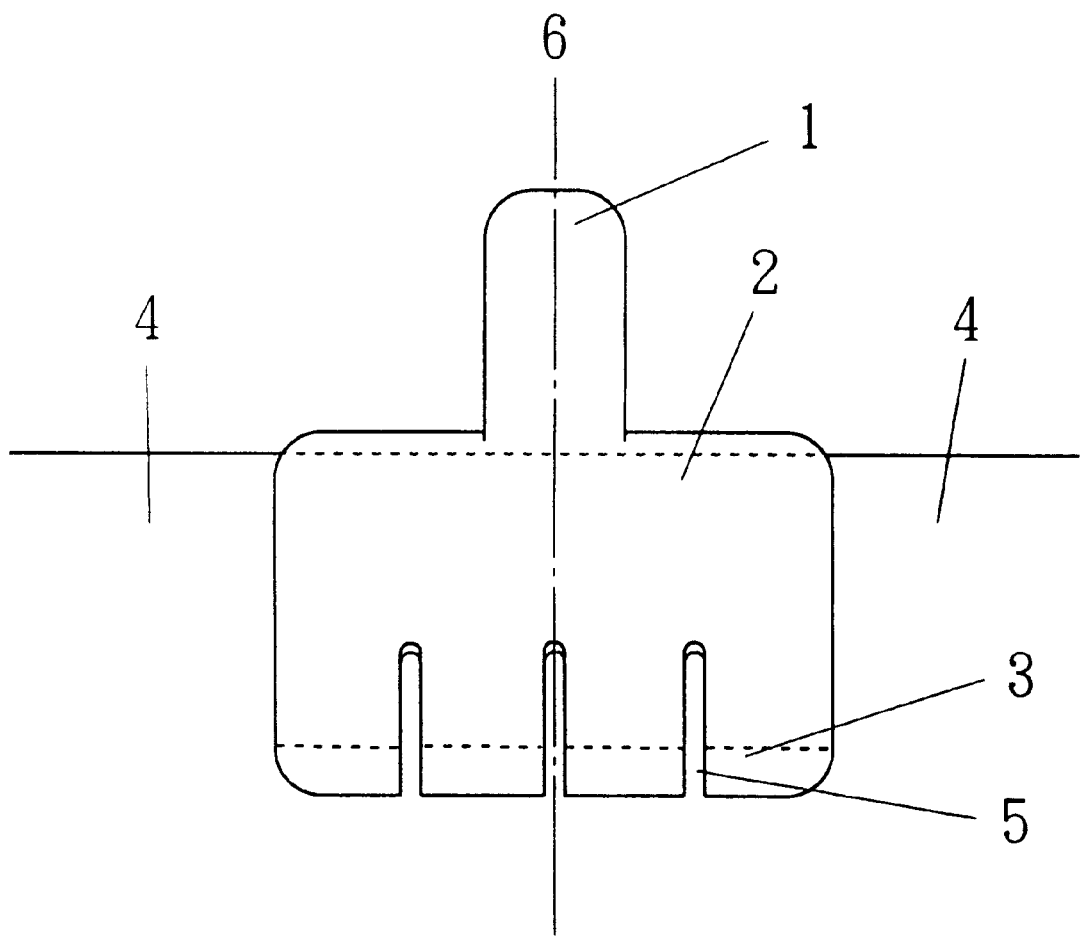
FIG. 2 is a lateral view of the oral implant of the present invention.
Figure 3:
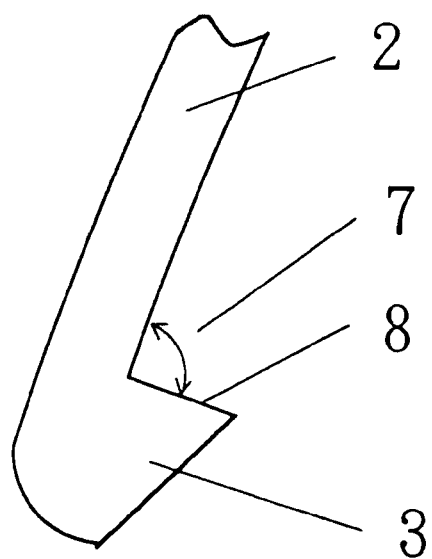
FIG. 3 is a cross-sectional view of a fixing hook at the top of the sheet portion of the oral implant of the present invention.

The sheet portion had the following dimensions: a thickness of about 0.5 mm, a crosswise dimension of 14 mm, and a longitudinal dimension of 7 mm. The notches 5 had the following dimensions: a length of 4 mm, an interval of 3 mm, and a width of 0.5 mm. The fixing hooks had the following dimensions: 1 mm for the length of the upper surface 8, and 90 degrees for the angle 7. The shape was the same as in FIGS. 1 and 2, and the length of the post portion was 7 mm.
2) Results (Performance Evaluation)

The resulting oral implant was secured on the alveolar bone by insertion of the fixing hooks into grooves bored in the lateral faces of the bone. In this state, stress was applied (in a direction about 45 degrees in relation to a perpendicular to the post portion in FIG. 1) with a press to a region near the center of the post portion of the oral implant thus manufactured to assess the adequacy of fitting, and it was found that the implant remained in place at 200 kg or less. It was thus confirmed that the resulting oral implant was adequately secured on the bone and could be used as a dental root.

Embodiment 2

An oral implant with a sheet portion whose shape on the bone side did not match the surface shape of the alveolar bone was fabricated by a superplastic forming technique in which pure titanium was used as the material for the oral implant and which was based on a method in which clay was attached in a thickness of about 0.5 mm to part of an image of the same bone as in embodiment 1.

The sheet portion, notches, fixing hooks, and post portion had the same dimensions as in embodiment 1. Bone cement was applied in a thickness of about 1 mm to the inside of the sheet portion, and the oral implant was secured on the alveolar bone by insertion of the fixing hooks into grooves bored in the lateral faces of the alveolar bone.

The adequacy of fitting was studied five hours later under the same conditions as in embodiment 1, and it was found that no shifting had occurred at 200 kg or less. It was thus confirmed that the resulting oral implant was adequately secured on the bone and could be used as a dental root.

Embodiment 3

An oral implant with a sheet portion whose shape on the bone side matched in an inverted convex-concave arrangement the surface shape of the alveolar bone was fabricated on the basis of the images of the same bone as in embodiment 1 by a superplastic forming technique in which pure titanium was used as the material for the oral implant.

The sheet portion, notches, fixing hooks, and post portion had the same dimensions as in embodiment 1. The oral implant was secured on the alveolar bone by insertion of the fixing hooks into grooves bored in the lateral faces of the bone.

The adequacy of fitting was studied under the same conditions as in embodiment 1, and it was found that no shifting had occurred at 200 kg or less. It was thus confirmed that the resulting oral implant was adequately secured on the bone and could be used as a dental root.

Embodiment 4

An oral implant with a sheet portion whose shape on the bone side did not match the surface shape of the alveolar bone was fabricated by a superplastic forming technique in which pure titanium was used as the material for the oral implant and which was based on a method in which clay was attached in a thickness of about 0.5 mm to part of an image of the same bone as in embodiment 1.

The sheet portion, notches, fixing hooks, and post portion had the same dimensions as in embodiment 1. Bone cement was applied in a thickness of about 1 mm to the inside of the sheet portion, and the oral implant was secured on the alveolar bone by insertion of the fixing hooks into grooves bored in the lateral faces of the alveolar bone.

The adequacy of fitting was studied five hours later under the same conditions as in embodiment 1, and it was found that no shifting had occurred at 200 kg or less. It was thus confirmed that the resulting oral implant was adequately secured on the bone and could be used as a dental root.

Embodiment 5

Based on the images of a canine alveolar bone, an oral implant with a sheet portion whose shape on the bone side matched in an inverted convex-concave arrangement the surface shape of the alveolar bone was implanted after being fabricated on the basis of the images of the alveolar bone by a superplastic forming technique in which pure titanium was used as the material for the oral implant.

The sheet portion had the following dimensions: a thickness of 0.5 mm, a crosswise dimension of 14 mm, and a longitudinal dimension of 7 mm. The notches 5 had the following dimensions: a length of 4 mm, an interval of 3 mm, and a width of 0.5 mm. The fixing hooks had the following dimensions: 1 mm for the length of the upper surface 8, and 90 degrees for the angle 7. The shape was the same as in FIGS. 1 and 2, and the length of the post portion was 7 mm.

The resulting oral implant was secured on the alveolar bone by insertion of the fixing hooks into grooves bored in the lateral faces of the bone. No inflammation or the like had occurred following implantation, and the implant could be used for three months or longer.

As described in detail above, the present invention relates to an oral implant comprising a sheet portion, fixing hooks, a post portion, and the like. According to the present invention, 1) the depth to which the oral implant is sunk into the alveolar bone during use can be reduced, and the unnecessary strain on the alveolar bone eliminated; 2) physical stress exerted on the patient during the implantation of the oral implant can thus be minimized, and the incidence of inflammation following implantation reduced; 3) the oral implant can be secured on the alveolar bone in a simple manner; 4) the use of an auxiliary pin provides better positioning of the implant on the alveolar bone and prevents the implant from falling off; 5) the implant can be secured without being embedded in the bone; and other remarkable effects can be demonstrated.

What is claimed is:

1. An oral implant, which is used by being secured on an alveolar bone, said oral implant comprising:

a sheet portion having an inverted convex-concave shape ending in edges such that said sheet portion extends over and down both sides of the alveolar bone when in use, said sheet portion being resilient so that it temporarily expands when said oral implant is snapped onto lateral faces of the alveolar bone;

fixing hooks provided on said edges of said sheet portion and designed for securing said oral implant on the alveolar bone and preventing said implant from falling off; and a post portion for mounting an artificial tooth.

2. The oral implant according to claim 1, further comprising an auxiliary pin for reinforced mounting on the alveolar bone.

3. An oral implant, which is used by being secured on an alveolar bone, said oral implant comprising:

a sheet portion having two sides and an opening therebetween such that said sheet portion extends over and down both sides of the alveolar bone when in use, said sheet portion being resilient so that it temporarily expands when said oral implant is snapped onto lateral faces of the alveolar bone;

fixing hooks provided on edges of said sheet portion and designed for securing said oral implant on the alveolar bone and preventing said implant from falling off; and a post portion for mounting an artificial tooth.

4. The oral implant according to claim 2, further comprising an auxiliary pin for reinforced mounting on the alveolar bone.

5. The oral implant according to claim 1 or 2, further comprising notches in lateral faces of said sheet portion.

* * * * *

UNITED STATES PATENT AND TRADEMARK OFFICE
CERTIFICATE OF CORRECTION

PATENT NO.    : 6,287,118 B1  
DATED         : September 11, 2001  
INVENTOR(S)   : Naganuma et al.

Page 1 of 1

It is certified that error appears in the above-identified patent and that said Letters Patent is hereby corrected as shown below:

<u>Title page,</u>
Item [75], the third inventor's name should read:

-- [75] Inventors: Katsuyoshi Naganuma; Akira Kamiya; Akira Watazu; Toru Nonami; Makoto Kato, all of Aichi (JP) --

Item [73], the Assignee's information should read:

-- [73] Assignee: Japan as represented by Director General of Agency of Industrial Science and Technology, Tokyo (JP) --

Signed and Sealed this

Eighteenth Day of June, 2002

*Attest:*

JAMES E. ROGAN
*Attesting Officer*    *Director of the United States Patent and Trademark Office*